United States Patent
Schrader et al.

(10) Patent No.: US 6,357,536 B1
(45) Date of Patent: Mar. 19, 2002

(54) METHOD AND APPARATUS FOR MEASURING FLUID DENSITY AND DETERMINING HOLE CLEANING PROBLEMS

(75) Inventors: Hartmut Schrader, Nienhagen; Frank Reiber, Didderse, both of (DE)

(73) Assignee: Baker Hughes, Inc., Houston, TX (US)

( * ) Notice: Subject to any disclaimer, the term of this patent is extended or adjusted under 35 U.S.C. 154(b) by 0 days.

(21) Appl. No.: 09/513,426

(22) Filed: Feb. 25, 2000

(51) Int. Cl.⁷ .............................................. E21B 49/08
(52) U.S. Cl. ........................................ 175/48; 166/264
(58) Field of Search ...................... 175/48, 50; 166/264, 166/100; 250/260, 265

(56) References Cited

U.S. PATENT DOCUMENTS

| | | |
|---|---|---|
| 3,602,322 A | 8/1971 | Gorsuch |
| 3,608,653 A | 9/1971 | Rehm |
| 3,760,891 A | 9/1973 | Gadbois |
| 4,412,130 A * | 10/1983 | Winters ...................... 250/260 |
| 4,440,239 A | 4/1984 | Evans |
| 4,535,851 A | 8/1985 | Kirkpatrick et al. |
| 5,622,223 A * | 4/1997 | Vasquez ...................... 166/264 |

* cited by examiner

Primary Examiner—Frank Tsay
(74) Attorney, Agent, or Firm—Madan, Mossman & Sriram, PC

(57) ABSTRACT

A drilling fluid analyzing apparatus has at least two sensors is used to analyze drilling fluid that contains cuttings. The sensors are mounted vertically spaced in a well riser and in communication with well return fluid. The sensors convert the pressure exerted by the return fluid to signals that are then conveyed to a processor. The processor determines the density of the return fluid, and the fluid density is indicative of borehole cleaning efficiency. Two additional sensors may be added to the drilling fluid input mud pipe to sense the pressure exerted by the drilling mud before it is contaminated with cuttings.

14 Claims, 4 Drawing Sheets

METHOD AND APPARATUS FOR MEASURING FLUID DENSITY AND DETERMINING HOLE CLEANING PROBLEMS

RELATED APPLICATIONS

This application is related to United States Application for Letters Patent Ser. No. 09/197,300 filed on Nov. 20, 1998.

BACKGROUND OF THE INVENTION

1. Field of the Invention

This invention relates to a method and system for continuously measuring the efficiency of drilling fluid. More specifically, the invention relates to a system and method for detecting cuttings accumulation and washout in wellbore during drilling operations by analyzing the return fluid containing drilling mud and cuttings exiting the wellbore.

2. Description of the Related Art

Drilling fluids are employed when drilling boreholes into subterranean formations. The drilling fluid "mud" consists of mixture of liquids and solids to provide special properties to better perform several primary functions in a drilling well. Drilling fluids lift the formation cuttings to the surface, control subsurface pressure, lubricate the drill string and bit, aid bottom-hole cleaning, aid formation evaluation, and provide protection to formation productivity.

One of the primary functions of the drilling fluid is the control of the formation pressure. The hydrostatic pressure exerted by the mud column, which is controlled by the density of the drilling fluid, is maintained above the pressure of the formation. If the formation pressure exceeds the pressure exerted by the mud column, formation fluid may enter the wellbore, causing a kick, which is any unscheduled entry of formation fluid into the wellbore. This results in a gain in the flow rate of the returning fluid. Additionally, the drilling fluid may incur losses due to the presence of a fracture in the formation. Fractures can result in loss of the drilling fluid, which results in a loss of the fluid flow rate at the surface. It is important to continuously monitor for the pressure of kicks and the fracture during drilling of wellbores. There are several methods and systems well known in the art that measure flow rate directly with various sensors.

Another primary purpose of the drilling fluid is to lift cuttings from the wellbore. The drilling mud is circulated down the drill string, through the bit, and returns to the surface through the annular space between the drill string and the wellbore wall. The mud returning to the surface is known as return fluid comprising drilling mud, formation particles called cuttings, and possibly some formation fluids. The drilled cuttings are picked up at the bit and returned to the surface for separation from the mud and for disposal. This removal of the drilled solids from the mud stream is critical to the subsequent reconditioning of the mud for recirculation in the well.

To control and improve drilling performance, evaluation of wellbore condition is important. Keeping the hole clean, especially in extended reach wells, is a key issue as cuttings accumulation in the annulus can contribute to, if not directly cause, pipe sticking and twist-offs. This is a concern when drilling a deviated well since a bed of cuttings is almost always formed on the lower side of the drill pipe. By measuring the cuttings discharge at the surface, the buildup of cuttings in the well can be detected early and remedial action taken to prevent a catastrophic failure.

Another obstacle encountered in drilling operations is washout. Washout is excessive borehole enlargement caused by solvent and erosion action by the drilling fluid. Washout can cause severe damage to the formation, contaminate the connate formation fluids, and waste costly drilling mud. Early detection through the measurement of cuttings exiting the wellbore can also help the mitigation of this problem.

In typical cuttings evaluation, the cuttings from the well are discharged over one or more shale shaker screens to separate them from the drilling mud, and all cuttings coming from the shakers are weighed. With expected cuttings density known by the user, the expected volume of the cuttings is calculated and the volume removed is compared to the volume calculated. Thus hole-cleaning efficiency is evaluated.

Currently the main types of mud out weight sensors used are a strain gauge and suspended heavy weight system, systems using differential pressure plates in the mud pit, and radioactive source sensors. Some of the mud adheres to the cuttings and is carried over with the cuttings discharged from the shale shaker. This portion of mud is lost to the mud system, which has been reported to be as high as two barrels of mud for every barrel of cuttings. The mud lost in the cuttings causes accuracy problems with the first two sensor types. The third system, although more accurate, is costly and requires certification and approval. The first two systems are not accurate enough for the cuttings removal performance application because of the settlement of the cuttings in the pits.

SUMMARY OF THE INVENTION

An object of the present invention is to provide an accurate, simple arid robust sensor system to evaluate hole cleaning performance. Two highly accurate pressure sensors are installed vertically displaced in a well riser to sense the pressure exerted by the return fluid including drilling mud and cuttings. Another object is to provide a processor for receiving signals from the sensors and for processing the data to determine hole cleaning performance. The advantage in measuring the return fluid is that the flow out including the cuttings is homogenous in the riser and no settlements occur.

In another embodiment, two additional sensors are provided to measure the drilling mud as it enters the well. With two sensors measuring return fluid pressure and two sensors measuring the pressure of drilling fluid entering the well, a processor can calculate efficiency based on more measured parameters. The processed data is an indication of well cleaning efficiency that can allow for early detection of washout or cuttings accumulation.

In another embodiment, sensors provided in a riser during tripping operations are used in conjunction with other sensors, such as flow rate sensors, to detect washouts and kick through the measurement of mud parameters entering the wellbore.

BRIEF DESCRIPTION OF THE DRAWINGS

For detailed understanding of the present invention, references should be made to the following detailed description of the preferred embodiment, taken in conjunction with the accompanying drawings, in which like elements have been given like numerals and wherein.

DESCRIPTION OF THE PREFERRED EMBODIMENT

Figure 1:
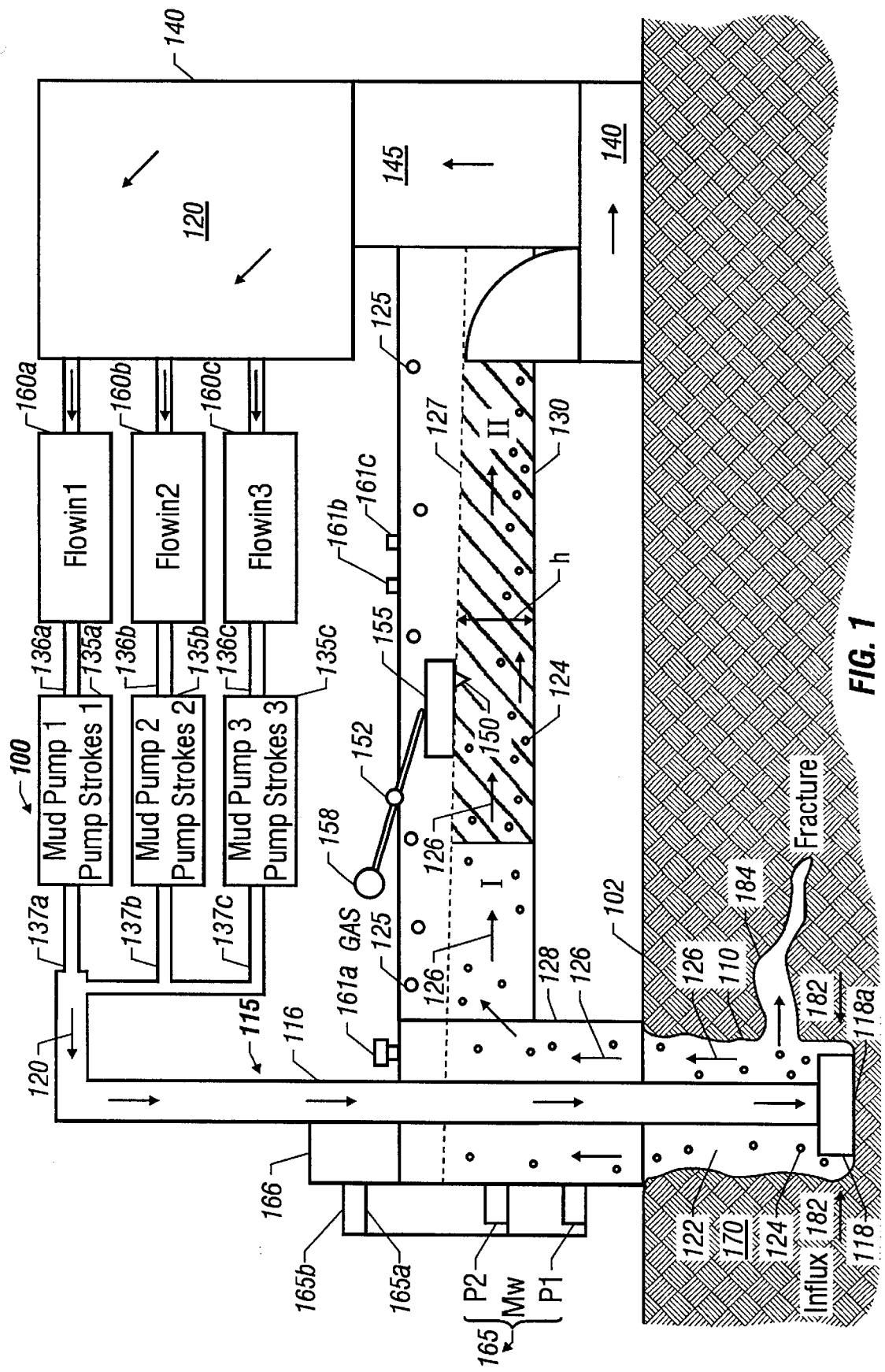
FIG. 1 is a schematic diagram of a drilling fluid flow measurement system for use during the drilling of a wellbore.

FIG. 1 is a schematic elevational diagram of a drilling fluid flow system 100. The system 100 shown includes a drill string 115 that includes a tubing 116 that has a drill bit 118 at its bottom end. To drill the wellbore 110, a drilling fluid 120 is pumped from a source (pit) 140 into the tubing 116 by one or more mud pumps 135a–135c. The drill bit 118 is rotated by a mud motor (not shown) and/or by rotating the tubing 116 at the surface by a suitable motor (not shown). The drill bit 118 cuts the rock into small fragments 124 (referred to in the art as the "cuttings"). The drilling fluid 120 discharges at the drill bit bottom 118a and returns to the surface 102 via the annular space 122 (also referred to as the annulus) carrying the cuttings 124. The returning drilling fluid is denoted by the numeral 126.

The returning drilling fluid 126 passes into a riser 128, and then into a generally horizontal out flow or return line 130. The flow line 130 has a sufficiently large cross-sectional area, which allows the returning fluid 126 to flow without filling the entire outflow line 130. This leaves sufficient area above the fluid level 127 for the installation of sensors 155. The fluid 126 returning from the wellbore may be a three phase fluid: liquid, gas and solids. Any gas flows above the fluid line 127. Some solids settle at the flow line 130. The fluid 126 from the return line 130 passes to a shaker that removes the cuttings 124. The fluid 126 is then processed in a processor 145 and passed to an active pit 140 that serves as the source of the clean fluid 120.

In the present invention, mud weight out sensor 165 is suitably installed in the riser 128, which provides measurements for determining the density of the fluid 126 returning into the flow line 130. The mud weight out sensor is preferably a set of two pressure sensors P2 and P1.

A separate flow in sensor is preferably installed to determine the output of each pump 135a–135c. In the system 100, sensors 160a–160c respectively placed in the in-flow lines 136a–136c provide fluid output of each of the pumps 135a–135c. Alternatively, the sensors 160a–160c may be installed in the output lines 137a–137c. Any suitable sensor may be used for measuring the flow through the pumps 135a–135c. Details of sensors such as these are detailed in the abovementioned related patent application, Ser. No. 09/197,300 filed on Nov. 20, 1998. The entire content of said application is hereby incorporated herein by reference.

As noted above, one of the primary functions of the drilling fluid 120 is the control of the formation pressure. The hydrostatic pressure exerted by the mud column 180 is maintained above the pressure of the formation 170. This is controlled by the density of the drilling fluid 120. Drilling fluids also contain a variety of additives. Drilling fluids are selected based on the desired characteristics relating to the density, viscosity, cutting carrying capacity, corrosion resistance, etc. Both water-based and oil-based drilling fluids are used depending upon the specific application. If the formation pressure exceeds the pressure exerted by the mud column 180, formation fluid 182 may enter the wellbore 110, causing a kick, which is any unscheduled entry of formation fluid into the wellbore 100. This results in a gain in the flow rate of the returning fluid 126. Additionally, the drilling fluid may incur losses due to the presence of a fracture in the formation 170, such as fracture 184. This results in loss of the drilling fluid, which results in a loss of the fluid flow rate at the surface. Monitoring of the flow rate of fluids entering and exiting the wellbore is accomplished with sensors 155 and 160a–160c.

As noted above, other key functions of the drilling fluid 120 keeping the wellbore 110 clean by removing cuttings 124, especially in extended reach wells, because cuttings accumulation in the annulus can contribute to, if not directly cause, pipe sticking and twist-offs. This is a concern when drilling a deviated well since a bed of cuttings is almost always formed on the lower side of the drill pipe. By measuring the cuttings discharge at the surface, the buildup of cuttings in the well can be detected early and remedial action taken to prevent a catastrophic failure.

Another obstacle encountered in drilling operations, as noted above, is washout. Washout is excessive enlargement of wellbore 110 caused by solvent and erosion action by the drilling fluid 120. Washout can cause severe damage to the formation, contaminate the connate formation fluids, and waste costly drilling mud. Early detection through the measurement of cuttings 124 exiting the wellbore 110 can also help mitigate this problem. The novelty of the present invention is that highly accurate and inexpensive measurements of pressure differentials in this relatively homogeneous returning fluid 122 including cuttings 124 can be made at the riser 128. This measurement can lead to the early detection of washouts and hole cleaning problems.

Mounted on the riser 128 weight-out sensor 165 are preferably two pressure sensors P2 and P1. These sensors are spaced vertically approximately two meters apart and are in communication with the returning fluid 126 so that the pressure exerted by the returning fluid can be detected and measured. Preferably, the sensors would have a measuring accuracy of 0.01% F.S. or better. The pressure sensors P2 and P1 convert the measured pressure to an electrical signal. This signal is then conveyed by conductors 165a and 165b to a processor 166 that performs an evaluation to determine the density of the returning fluid including cuttings 124.

Figure 2:
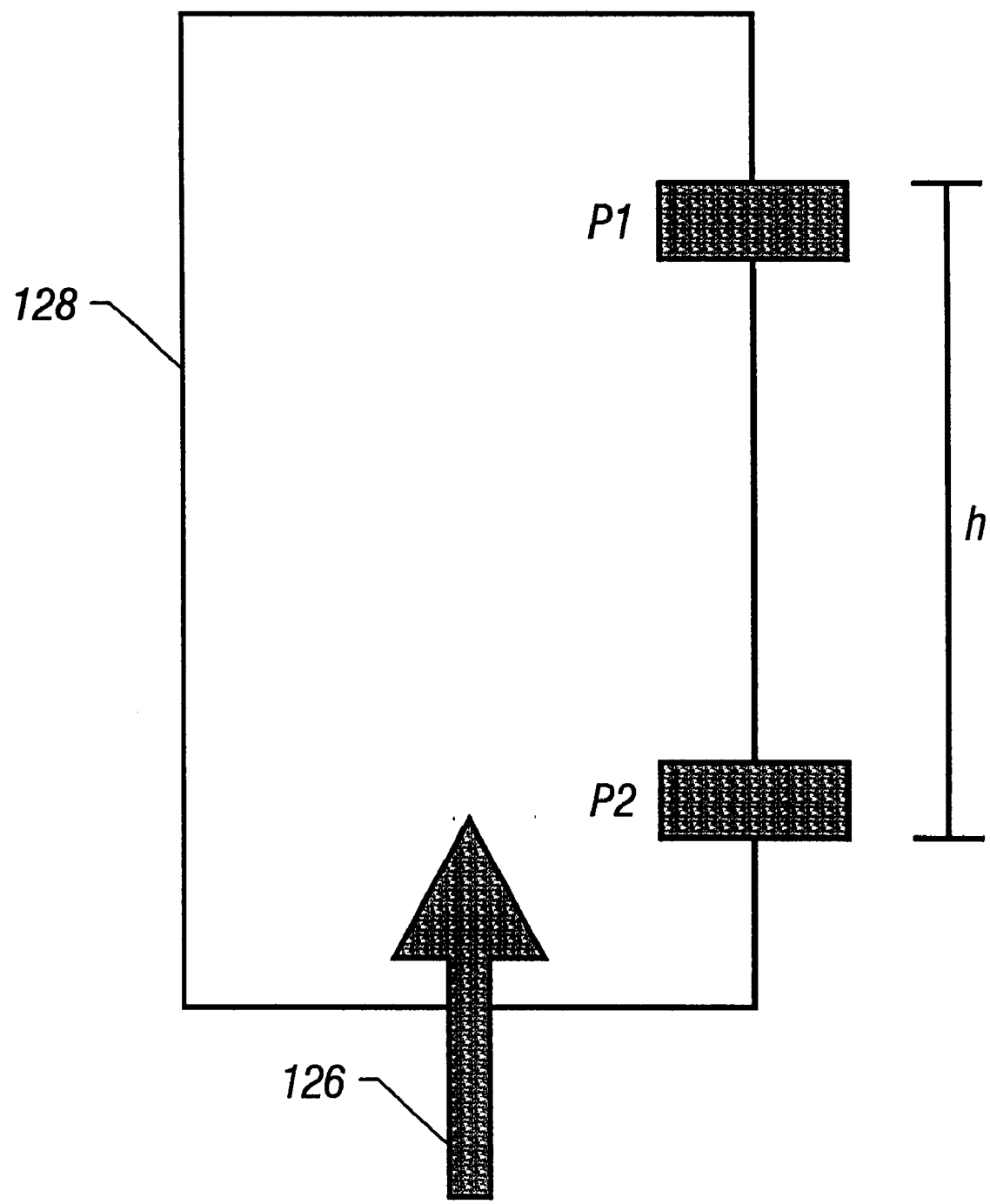
FIG. 2 is a simplified schematic used to show the relationship between variables used in calculating mud density and the present invention.

The dynamic pressure losses over a length interval of approximately two meters can be neglected. The measured pressure values can be evaluated to determine a highly accurate mud out weight including the cuttings 124. Referring now to schematic in FIG. 2, with the measured pressures P1, P2, the known vertical separation h of the sensors, and g being the earth gravitational force the mud weight out ñ can be calculated by processor 166 with equation 1.

$$\rho_{out} = \frac{P2 - P1}{gh} \qquad \text{(Equation 1)}$$

Knowing the mud weight out, the weight of the removed cuttings can now be calculated with the measured flow out and the flow in over the measured mud weight in and mud weight out. This weight is compared with the expected weight of the cuttings calculated with the known cross section of the bit 118, rate of penetration and the cuttings density. A cutre factor K is determined as the relation between the measured cuttings weight and the expected cuttings weight, and can be calculated with equation 2:

$$K = 4\left[\frac{q_{out}\rho_{out} - q_{in}\rho_{in}}{ROP * OD^2 \pi \rho_{cuttings}}\right] \quad \text{(Equation 2)}$$

Where:
ROP=rate of penetration;
OD=bit outer diameter;
ρ=density;
q=flow rate; and
K=cutre factor.

The cutre factor indicates wash out and hole cleaning problems by K>1 indicating wash out problems and K<1 hole indicating cleaning problems (cuttings accumulation).

If the flow out is not measured and no influxes or losses occur, the flow out can be set equal to the flow in for equation 1. For even higher accuracy, the algorithm must take care of circulation lag times, and practical application will dictate if and how the signals must be averaged or filtered.

Figure 3:
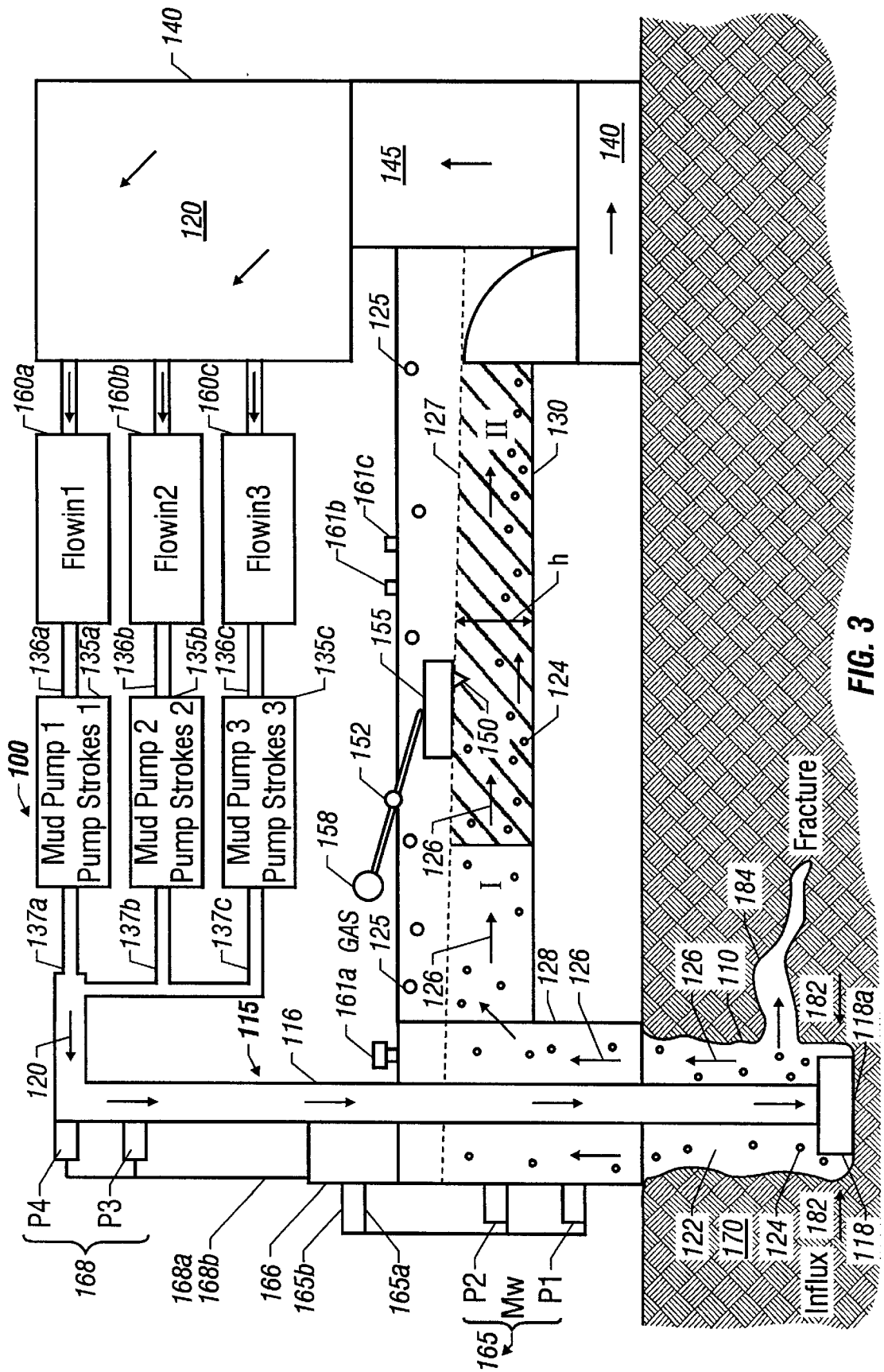
FIG. 3 is a schematic diagram of a drilling fluid flow measurement system for use during the drilling of a wellbore wherein an additional sensor is added to a vertical inflow line.

In an alternate embodiment is shown in FIG. 3, return fluid 126 is removed from the borehole 110 and flows through the riser 128 as in the first described embodiment. As in the first embodiment, weight-out sensor 165 comprising pressure sensors P1 and P2 detect the return fluid pressure and pass the information to the processor 166 for evaluation. In this embodiment, drilling fluid 120 is evaluated using a mud weight-in sensor 168 comprising preferably two pressure sensors P4 and P3. Mud pumps 135a–135c pump the drilling fluid 120 from an active pit 140, and the fluid flows through inflow lines 136a–136c, through one or more mud pumps 135a–135c, and through output lines 137a–137c before being passed back into wellbore 110 through tube 116. Prior to being injected back into wellbore 110, the drilling fluid passes sensors P4 and P3 of weight-in sensor 168. The sensors P4 and P3 are spaced vertically approximately two meters apart and are in communication with the drilling fluid 120 so that the pressure exerted by the drilling fluid 120 can be detected and measured. The pressure sensors P4 and P3 convert the measured pressure to an electrical signal. Conductors 168a and 168b convey this signal to the processor 166 that performs the evaluation of the drilling fluid 120 along with the evaluation of the returning fluid 126. The actual location of the sensors P4 and P3 is not critical, so sensors P4 and P3 may be located on any oil well drilling component through which drilling mud passes. However, the chosen location must allow for vertical displacement of the sensors.

Figure 4:
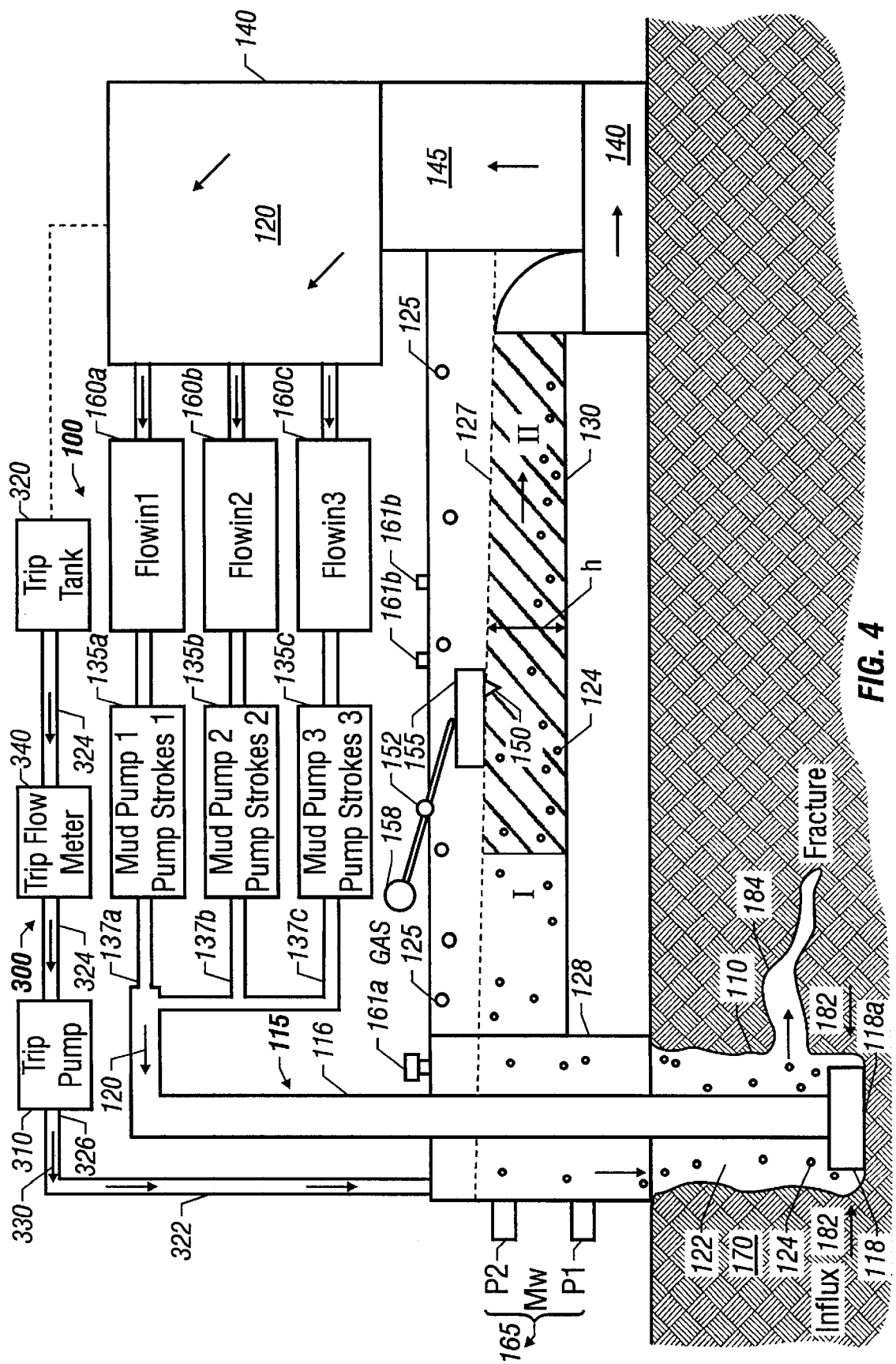
FIG. 4 is the system of FIG. 1 with a secondary pump during tripping operation and an associated mud weight sensor according to the present invention for determining mud weight entering the wellbore.

FIG. 4 shows the system 100 of FIG. 1 with a secondary fluid inflow system 300. This secondary or trip inflow system includes a secondary pump or trip pump 310 that pumps drilling fluid 330 from a trip tank 320 into the annulus 122 of the wellbore 110 via a supply line 322. The trip pump 310 is usually much smaller than the main mud pumps 135a–135c because the fluid volume pumped in during tripping is relatively small. The trip pump 310 may be arranged to pump fluid from the tank 120, eliminating the need for a separate trip tank 320. A flow measuring apparatus 340 (also referred to herein as a trip flow meter) is connected in line 324 between the trip tank 320 and the trip pump 340. The trip flow meter may also be installed in the horizontal section 326 of the line 322. The flow meter 340 provides the volume of the fluid pumped into the wellbore 110 during the tripping operation. In this alternate embodiment of the present invention, mud weight sensors 165 are utilized to determine the weight of the mud 330 being pumped into the wellbore annulus 122. With the mud weight Mw measured along with the flow rate and the rate and volume of the drill string filled with mud being known, changes in the expected mud parameters are determinable. Changes in fluid volume and pressure entering the well can be used to indicate the presence of washouts or a kick. Appropriate actions may then be taken to preserve the formation and ensure safety of the operation.

The foregoing description is directed to particular embodiments of the present invention for the purpose of illustration and explanation. It will be apparent, however, to one skilled in the art that many modifications and changes to the embodiment set forth above are possible without departing from the scope and the spirit of the invention. It is intended that the following claims be interpreted to embrace all such modifications and changes.

What is claimed is:

1. A fluid density monitoring system for use in a drilling system having an inflow line supplying drilling fluid under pressure into a wellbore and a riser carrying a return fluid including said drilling fluid and cuttings returning from the wellbore, said fluid monitoring system comprising a sensor assembly disposed in said riser, said sensor assembly providing measurements representative of the density of the return fluid flowing through said riser.

2. The fluid density monitoring system of claim 1 wherein said sensor assembly comprises at least two sensors.

3. The fluid density monitoring system of claim 2 wherein said at least two sensors are pressure sensors and where said density is related to a pressure differential between said pressure sensors.

4. The fluid density monitoring system of claim 1 further comprising a processor for determining wellbore cleaning efficiency of said drilling fluid.

5. The fluid density monitoring system of claim 4 wherein said efficiency is determined by a relationship between fluid density in said inflow line and fluid density in said riser, said efficiency being indicative of washouts and hole cleaning problems.

6. The fluid density monitoring system of claim 1 wherein said sensor assembly is a first sensor assembly and further comprising a second sensor assembly disposed in said inflow line.

7. The fluid density monitoring system of claim 6 wherein said first sensor assembly further comprises at least two sensors and said second sensor assembly further comprises at least two sensors.

8. The fluid density monitoring system of claim 7 wherein said sensors are all pressure sensors and where said density of said return fluid is related to a pressure differential between said pressure sensors disposed on said riser and said density of inflow line fluid is related to a pressure differential between said pressure sensors disposed in said inflow line.

9. The fluid density monitoring system of claim 6 further comprising a processor for determining wellbore cleaning efficiency of said drilling fluid.

10. The fluid density monitoring system of claim 9 wherein said efficiency is determined by a relationship between fluid density in said inflow line and return fluid density in said riser, said efficiency being indicative of washouts and hole cleaning problems.

11. A method of determining a parameter of interest of a drilling system having an inflow line supplying fluid under pressure into a wellbore and a riser carrying return fluid containing cuttings returning from the wellbore, the method comprising:

(a) sensing the pressure exerted by return fluid with a sensor, said sensor being disposed and vertically spaced in said riser and in communication with said return fluid;

(b) converting said sensed pressure to a signal indicative of the pressures sensed; and (c) processing said signal with a processor to determine the density of said fluid, said fluid density being indicative of said borehole cleaning efficiency.

12. The method of claim 11 wherein said sensor is at least two sensors separated by a vertical distance h, said at least two sensors providing pressure indications P1 and P2.

13. The method of claim 12 further comprising computing the density $\rho_{out}$ of said return fluid with said processor whereby $\rho_{out}$=(P2-P1)/(g*h), said g being the value of gravitational force.

14. The method of claim 13 further comprising entering a value for rate of penetration ROP in said processor, entering the outer diameter OD of a drill bit used for drilling the wellbore in the processor, entering density of inflow line fluid Pin in said processor, entering flow rates qin and qout in said processor for fluid entering and leaving said wellbore, and computing a cleaning efficiency K of said fluid with said processor whereby:

$$K = 4\left[\frac{q_{out}\rho_{out} - q_{in}\rho_{in}}{ROP * OD^2 \pi \rho_{cuttings}}\right].$$

* * * * *